(12) United States Patent
Felix et al.

(10) Patent No.: US 12,369,828 B1
(45) Date of Patent: *Jul. 29, 2025

(54) EXTENDED WEAR AMBULATORY ELECTROCARDIOGRAMAY MONITOR

(71) Applicant: Bardy Diagnostics, Inc., Bellevue, WA (US)

(72) Inventors: Jason Felix, Vashon Island, WA (US); Jon Mikalson Bishay, Lexington, KY (US); Gust H. Bardy, Carnation, WA (US)

(73) Assignee: Bardy Diagnostics, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/212,237

(22) Filed: May 19, 2025

Related U.S. Application Data

(63) Continuation of application No. 18/353,407, filed on Jul. 17, 2023, now Pat. No. 12,310,735, which is a
(Continued)

(51) Int. Cl.
*A61B 5/05* (2021.01)
*A61B 5/00* (2006.01)
(Continued)

(52) U.S. Cl.
CPC ............ *A61B 5/282* (2021.01); *A61B 5/0006* (2013.01); *A61B 5/0022* (2013.01);
(Continued)

(58) Field of Classification Search
CPC ................. A61B 5/282; A61B 5/0006; A61B 2560/0412; A61B 5/6833; A61B 5/259; A61B 5/28; A61B 5/1118; A61B 5/1117; A61B 2560/0468; A61B 5/02405; A61B 5/256; A61B 5/6804
(Continued)

(56) References Cited

U.S. PATENT DOCUMENTS 3,215,136 A 11/1965 Holter et al.
3,569,852 A 3/1971 Berkovits
(Continued)

FOREIGN PATENT DOCUMENTS

DE 19955211 5/2001
EP 1859833 11/2007
(Continued)

OTHER PUBLICATIONS

US 6,527,714 B2, 03/2003, Bardy (withdrawn)
(Continued)

*Primary Examiner* — Joseph A Stoklosa
*Assistant Examiner* — Brian M Antiskay
(74) *Attorney, Agent, or Firm* — K&L Gates LLP

(57) ABSTRACT

An electrocardiography monitor is provided. A sealed housing includes one end wider than an opposite end of the sealed housing. Electronic circuitry is provided within the sealed housing. The electronic circuitry includes an electrographic front end circuit to sense electrocardiographic signals and a micro-controller interfaced to the electrocardiographic front end circuit to sample the electrocardiographic signals. A buzzer within the housing outputs feedback to a wearer of the sealed housing.

20 Claims, 6 Drawing Sheets

Related U.S. Application Data continuation of application No. 17/691,004, filed on Mar. 9, 2022, now Pat. No. 11,701,045, which is a continuation of application No. 16/684,386, filed on Nov. 14, 2019, now Pat. No. 11,272,872, which is a continuation of application No. 15/676,896, filed on Aug. 14, 2017, now Pat. No. 10,478,083, which is a continuation of application No. 14/080,725, filed on Nov. 14, 2013, now Pat. No. 9,730,593.

(60) Provisional application No. 61/882,403, filed on Sep. 25, 2013.

(51) Int. Cl.
*A61B 5/0205* (2006.01)
*A61B 5/11* (2006.01)
*A61B 5/259* (2021.01)
*A61B 5/282* (2021.01)
*A61B 5/316* (2021.01)
*A61B 5/335* (2021.01)
*A61B 5/349* (2021.01)
*A61B 5/35* (2021.01)
*A61B 5/01* (2006.01)
*A61B 5/021* (2006.01)
*A61B 5/08* (2006.01)
*A61B 5/087* (2006.01)
*A61B 5/091* (2006.01)
*A61B 5/145* (2006.01)
*A61B 5/1455* (2006.01)
*G01N 27/30* (2006.01)

(52) U.S. Cl.
CPC ........ *A61B 5/02055* (2013.01); *A61B 5/1116* (2013.01); *A61B 5/1117* (2013.01); *A61B 5/1118* (2013.01); *A61B 5/259* (2021.01); *A61B 5/316* (2021.01); *A61B 5/335* (2021.01); *A61B 5/349* (2021.01); *A61B 5/35* (2021.01); *A61B 5/4809* (2013.01); *A61B 5/6801* (2013.01); *A61B 5/6823* (2013.01); *A61B 5/6833* (2013.01); *A61B 5/01* (2013.01); *A61B 5/021* (2013.01); *A61B 5/0816* (2013.01); *A61B 5/087* (2013.01); *A61B 5/091* (2013.01); *A61B 5/14532* (2013.01); *A61B 5/14542* (2013.01); *A61B 5/14551* (2013.01); *A61B 5/7455* (2013.01); *A61B 2505/07* (2013.01); *A61B 2560/0271* (2013.01); *A61B 2560/0412* (2013.01); *A61B 2560/045* (2013.01); *A61B 2562/0219* (2013.01); *A61B 2562/164* (2013.01); *G01N 27/307* (2013.01)

(58) Field of Classification Search
USPC ....... 600/372, 382, 384, 386, 388, 390–393, 600/508–509
See application file for complete search history.

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,506,678 A | 3/1985 | Russell et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,763,660 A | 8/1988 | Kroll et al. |
| 4,788,983 A | 12/1988 | Brink et al. |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,312,446 A | 5/1994 | Holschbach et al. |
| 5,314,453 A | 5/1994 | Jeutter |
| 5,331,966 A | 7/1994 | Bennett et al. |
| 5,333,615 A | 8/1994 | Craelius et al. |
| 5,341,806 A | 8/1994 | Gadsby et al. |
| 5,348,008 A | 9/1994 | Bornn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sandford et al. |
| 5,458,141 A | 10/1995 | Neil |
| 5,473,537 A | 12/1995 | Glazer et al. |
| 5,479,922 A | 1/1996 | Reichl |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olson et al. |
| 5,788,633 A | 8/1998 | Mahoney |
| 5,817,151 A | 10/1998 | Olson et al. |
| 5,819,741 A | 10/1998 | Karlsson et al. |
| 5,850,920 A | 12/1998 | Gilman et al. |
| 5,860,918 A | 1/1999 | Schradi et al. |
| 5,862,803 A | 1/1999 | Besson et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,956,013 A | 9/1999 | Raj et al. |
| 5,957,857 A | 9/1999 | Hartley |
| 5,984,102 A | 11/1999 | Tay |
| 5,987,352 A | 11/1999 | Klein et al. |
| 6,032,064 A | 2/2000 | Devlin et al. |
| 6,038,469 A | 3/2000 | Karlsson et al. |
| 6,101,413 A | 8/2000 | Olson et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,185,452 B1 | 2/2001 | Schulman et al. |
| 6,188,407 B1 | 2/2001 | Smith et al. |
| 6,223,080 B1 | 4/2001 | Thompson |
| D443,063 S | 5/2001 | Pisani et al. |
| 6,238,338 B1 | 5/2001 | DeLuca et al. |
| 6,245,025 B1 | 6/2001 | Torok et al. |

(56) References Cited

U.S. PATENT DOCUMENTS

| | | |
|---|---|---|
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |
| 6,434,410 B1 | 8/2002 | Cordero |
| 6,450,845 B1 | 9/2002 | Snyder et al. |
| 6,454,708 B1 | 9/2002 | Ferguson et al. |
| 6,456,256 B1 | 9/2002 | Amundson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura et al. |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,052,472 B1 | 5/2006 | Miller et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,197,357 B2 | 3/2007 | Istvan et al. |
| 7,206,630 B1 | 4/2007 | Tarler |
| 7,212,849 B2 | 5/2007 | Zhang et al. |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bornzin et al. |
| D558,882 S | 1/2008 | Brady et al. |
| 7,328,061 B2 | 2/2008 | Rowlandson et al. |
| 7,395,106 B2 | 7/2008 | Ryu et al. |
| 7,412,395 B2 | 8/2008 | Rowlandson et al. |
| 7,429,938 B1 | 9/2008 | Corndorf |
| 7,468,032 B2 | 12/2008 | Stahmann et al. |
| 7,552,031 B2 | 6/2009 | Vock et al. |
| D606,656 S | 12/2009 | Kobayashi et al. |
| 7,672,714 B2 | 3/2010 | Kuo et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,150,502 B2 | 4/2012 | Kumar et al. |
| 8,160,682 B2 | 4/2012 | Kumar et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,214,007 B2 | 7/2012 | Baker et al. |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegel et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,315,695 B2 | 11/2012 | Sebelius et al. |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,483,809 B2 | 7/2013 | Kim et al. |
| 8,538,503 B2 | 9/2013 | Kumar et al. |
| 8,545,416 B1 | 10/2013 | Kayyali et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,611,980 B2 | 12/2013 | Choe et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,630,699 B2 | 1/2014 | Baker et al. |
| 8,647,268 B2 | 2/2014 | Tran |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,742 B2 | 5/2014 | Beck et al. |
| 8,718,752 B2 | 5/2014 | Libbus et al. |
| 8,744,561 B2 | 6/2014 | Fahey |
| 8,750,974 B2 | 6/2014 | Baker et al. |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,858,432 B2 | 10/2014 | Robertson et al. |
| 8,926,509 B2 | 1/2015 | Magar et al. |
| 8,938,287 B2 | 1/2015 | Felix et al. |
| 8,948,935 B1 | 2/2015 | Peeters et al. |
| 8,965,492 B2 | 2/2015 | Baker et al. |
| 9,066,664 B2 | 6/2015 | Karjalainen |
| 9,135,608 B2 | 9/2015 | Herlitz |
| 9,149,229 B1 | 10/2015 | Tarler |
| 9,155,484 B2 | 10/2015 | Baker et al. |
| 9,204,813 B2 | 12/2015 | Kaib et al. |
| 9,211,073 B2 | 12/2015 | Banet et al. |
| 9,241,649 B2 | 1/2016 | Kumar et al. |
| 9,259,154 B2 | 2/2016 | Miller et al. |
| 9,277,864 B2 | 3/2016 | Yang et al. |

(56) References Cited

U.S. PATENT DOCUMENTS

| | | |
|---|---|---|
| 9,339,202 B2 | 5/2016 | Brockway et al. |
| 9,375,179 B2 | 6/2016 | Schultz et al. |
| 9,414,786 B1 | 8/2016 | Brockway et al. |
| 9,433,366 B2 | 9/2016 | Baker et al. |
| 9,439,566 B2 | 9/2016 | Arne et al. |
| 9,510,755 B2 | 12/2016 | Fong et al. |
| 9,603,542 B2 | 3/2017 | Veen et al. |
| 9,669,212 B2 | 6/2017 | Mueller et al. |
| 9,693,732 B1 | 7/2017 | Tarler |
| 9,700,222 B2 | 7/2017 | Quinlan et al. |
| 9,770,182 B2 | 9/2017 | Bly et al. |
| 9,877,663 B2 | 1/2018 | Baker et al. |
| 10,034,614 B2 | 7/2018 | Edic et al. |
| 10,045,708 B2 | 8/2018 | Dusan |
| 10,049,182 B2 | 8/2018 | Chefles et al. |
| 10,159,422 B2 | 12/2018 | Baker et al. |
| 10,271,754 B2 | 4/2019 | Bahney et al. |
| 10,327,660 B2 | 6/2019 | Gallego et al. |
| 10,405,799 B2 | 9/2019 | Kumar et al. |
| 10,413,251 B2 | 9/2019 | Golda et al. |
| 10,441,185 B2 | 10/2019 | Rogers et al. |
| 10,517,500 B2 | 12/2019 | Kumar et al. |
| 10,555,683 B2 | 2/2020 | Bahney et al. |
| 10,939,839 B2 | 3/2021 | Baker et al. |
| 11,051,743 B2 | 7/2021 | Felix et al. |
| 11,116,447 B2 | 9/2021 | Yang et al. |
| 11,141,091 B2 | 10/2021 | Kumar et al. |
| 11,445,967 B2 | 9/2022 | Felix et al. |
| 11,627,902 B2 | 4/2023 | Bahney et al. |
| 2001/0051766 A1 | 12/2001 | Gazdzinski |
| 2002/0013538 A1 | 1/2002 | Teller |
| 2002/0013717 A1 | 1/2002 | Ando et al. |
| 2002/0016798 A1 | 2/2002 | Sakai et al. |
| 2002/0072682 A1 | 6/2002 | Hopman |
| 2002/0082867 A1 | 6/2002 | MacCarter et al. |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0149349 A1 | 8/2003 | Jensen |
| 2003/0174881 A1 | 9/2003 | Simard et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0043640 A1 | 2/2005 | Chang |
| 2005/0058701 A1 | 3/2005 | Gross et al. |
| 2005/0096513 A1 | 5/2005 | Ozguz et al. |
| 2005/0096717 A1 | 5/2005 | Bishay et al. |
| 2005/0101875 A1 | 5/2005 | Semler et al. |
| 2005/0108055 A1 | 5/2005 | Ott et al. |
| 2005/0113661 A1 | 5/2005 | Nazeri et al. |
| 2005/0137485 A1 | 6/2005 | Cao et al. |
| 2005/0151640 A1 | 7/2005 | Hastings |
| 2005/0154267 A1 | 7/2005 | Bardy |
| 2005/0154294 A1 | 7/2005 | Uchiyama et al. |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030781 A1 | 2/2006 | Shennib |
| 2006/0030904 A1 | 2/2006 | Quiles |
| 2006/0041201 A1 | 2/2006 | Behbehani et al. |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0111943 A1 | 5/2006 | Wu |
| 2006/0122469 A1 | 6/2006 | Martel |
| 2006/0124193 A1 | 6/2006 | Orr et al. |
| 2006/0167502 A1 | 7/2006 | Haefner |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0029961 A1 | 2/2007 | Harita et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0088419 A1 | 4/2007 | Fiorina et al. |
| 2007/0088429 A1 | 4/2007 | Thompson |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0142722 A1 | 6/2007 | Chang |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0233198 A1 | 10/2007 | Ghanem et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0270678 A1 | 11/2007 | Fadem |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293742 A1 | 12/2007 | Bardy |
| 2007/0299325 A1 | 12/2007 | Farrell et al. |
| 2007/0299617 A1 | 12/2007 | Willis |
| 2008/0027337 A1 | 1/2008 | Dugan |
| 2008/0027339 A1 | 1/2008 | Nagai et al. |
| 2008/0051668 A1 | 2/2008 | Bardy |
| 2008/0058661 A1 | 3/2008 | Bardy |

(56) References Cited

U.S. PATENT DOCUMENTS

| | | |
|---|---|---|
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0143080 A1 | 6/2008 | Burr |
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0243012 A1 | 10/2008 | Fujihashi et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0309481 A1 | 12/2008 | Tanaka et al. |
| 2008/0312522 A1 | 12/2008 | Rowlandson et al. |
| 2009/0009342 A1 | 1/2009 | Karjalainen |
| 2009/0012412 A1 | 1/2009 | Wiesel |
| 2009/0012979 A1 | 1/2009 | Bateni et al. |
| 2009/0054737 A1 | 2/2009 | Magar et al. |
| 2009/0054952 A1 | 2/2009 | Glukhovsky et al. |
| 2009/0062670 A1 | 3/2009 | Sterling et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0093687 A1 | 4/2009 | Telfort et al. |
| 2009/0099469 A1 | 4/2009 | Flores |
| 2009/0112116 A1 | 4/2009 | Lee et al. |
| 2009/0131759 A1 | 5/2009 | Sims et al. |
| 2009/0133047 A1 | 5/2009 | Lee et al. |
| 2009/0156908 A1 | 6/2009 | Belalcazar et al. |
| 2009/0177073 A1 | 7/2009 | Sonnenborg |
| 2009/0182204 A1 | 7/2009 | Semler et al. |
| 2009/0216132 A1 | 8/2009 | Orbach |
| 2009/0264792 A1 | 10/2009 | Mazar |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2009/0327715 A1 | 12/2009 | Smith et al. |
| 2010/0007413 A1 | 1/2010 | Herleikson et al. |
| 2010/0022897 A1 | 1/2010 | Parker et al. |
| 2010/0056877 A1 | 3/2010 | Fein et al. |
| 2010/0056881 A1 | 3/2010 | Libbus et al. |
| 2010/0076517 A1 | 3/2010 | Imran |
| 2010/0081913 A1 | 4/2010 | Cross et al. |
| 2010/0137694 A1 | 6/2010 | Irazoqui et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234697 A1 | 9/2010 | Walter et al. |
| 2010/0234715 A1 | 9/2010 | Shin et al. |
| 2010/0234716 A1 | 9/2010 | Engel |
| 2010/0268103 A1 | 10/2010 | McNamara et al. |
| 2010/0280366 A1 | 11/2010 | Arne et al. |
| 2010/0298720 A1 | 11/2010 | Potkay |
| 2010/0312188 A1 | 12/2010 | Robertson et al. |
| 2010/0317957 A1 | 12/2010 | Lee et al. |
| 2010/0324384 A1 | 12/2010 | Moon et al. |
| 2010/0324405 A1 | 12/2010 | Niemi et al. |
| 2011/0009729 A1 | 1/2011 | Shin et al. |
| 2011/0021937 A1 | 1/2011 | Hugh et al. |
| 2011/0054285 A1 | 3/2011 | Searle et al. |
| 2011/0054286 A1 | 3/2011 | Crosby et al. |
| 2011/0060215 A1 | 3/2011 | Tupin, Jr. et al. |
| 2011/0066041 A1 | 3/2011 | Pandia et al. |
| 2011/0077497 A1 | 3/2011 | Oster et al. |
| 2011/0082842 A1 | 4/2011 | Groseclose, Jr. et al. |
| 2011/0105861 A1 | 5/2011 | Derchak et al. |
| 2011/0112379 A1 | 5/2011 | Li et al. |
| 2011/0125040 A1 | 5/2011 | Crawford et al. |
| 2011/0144470 A1 | 6/2011 | Mazar et al. |
| 2011/0160548 A1 | 6/2011 | Forster |
| 2011/0160601 A1 | 6/2011 | Wang et al. |
| 2011/0208076 A1 | 8/2011 | Fong et al. |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2011/0313305 A1 | 12/2011 | Rantala |
| 2012/0003933 A1 | 1/2012 | Baker et al. |
| 2012/0029300 A1 | 2/2012 | Paquet |
| 2012/0029306 A1 | 2/2012 | Paquet et al. |
| 2012/0029307 A1 | 2/2012 | Paquet et al. |
| 2012/0029309 A1 | 2/2012 | Paquet et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0079127 A1 | 3/2012 | Hadland |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0108993 A1 | 5/2012 | Gordon et al. |
| 2012/0158075 A1 | 6/2012 | Kaib et al. |
| 2012/0165645 A1 | 6/2012 | Russell et al. |
| 2012/0172695 A1 | 7/2012 | Ko et al. |
| 2012/0179665 A1 | 7/2012 | Baarman et al. |
| 2012/0184207 A1 | 7/2012 | Gaines |
| 2012/0215123 A1 | 8/2012 | Kumar et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0265080 A1 | 10/2012 | Yu et al. |
| 2012/0265738 A1 | 10/2012 | Beckmann et al. |
| 2012/0302906 A1 | 11/2012 | Felix et al. |
| 2012/0306662 A1 | 12/2012 | Vosch et al. |
| 2012/0323098 A1 | 12/2012 | Moein et al. |
| 2012/0323132 A1 | 12/2012 | Warner et al. |
| 2012/0330126 A1 | 12/2012 | Hoppe et al. |
| 2013/0041272 A1 | 2/2013 | Guillén Arredondo et al. |
| 2013/0077263 A1 | 3/2013 | Oleson et al. |
| 2013/0079611 A1 | 3/2013 | Besko |
| 2013/0079618 A1 | 3/2013 | Sandmore et al. |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0124891 A1 | 5/2013 | Donaldson |
| 2013/0131530 A1 | 5/2013 | Brockway et al. |
| 2013/0158361 A1 | 6/2013 | Bardy |
| 2013/0172763 A1 | 7/2013 | Wheeler |
| 2013/0197380 A1 | 8/2013 | Oral et al. |

(56) References Cited

U.S. PATENT DOCUMENTS

| | | |
|---|---|---|
| 2013/0225963 A1 | 8/2013 | Kodandaramaiah et al. |
| 2013/0225966 A1 | 8/2013 | Macia Barber et al. |
| 2013/0225967 A1 | 8/2013 | Esposito |
| 2013/0226018 A1 | 8/2013 | Kumar et al. |
| 2013/0231947 A1 | 9/2013 | Shusterman |
| 2013/0243105 A1 | 9/2013 | Lei et al. |
| 2013/0274565 A1 | 10/2013 | Langer et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0002234 A1 | 1/2014 | Alwan |
| 2014/0005502 A1 | 1/2014 | Klap et al. |
| 2014/0012154 A1 | 1/2014 | Mazar |
| 2014/0031663 A1 | 1/2014 | Gallego |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0121557 A1 | 5/2014 | Gannon et al. |
| 2014/0140359 A1 | 5/2014 | Kalevo et al. |
| 2014/0148718 A1 | 5/2014 | Stickney et al. |
| 2014/0180027 A1 | 6/2014 | Buller |
| 2014/0189928 A1 | 7/2014 | Oleson et al. |
| 2014/0194760 A1 | 7/2014 | Albert |
| 2014/0206977 A1 | 7/2014 | Bahney et al. |
| 2014/0213937 A1 | 7/2014 | Bianchi et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0280027 A1 | 9/2014 | Cordes et al. |
| 2014/0296651 A1 | 10/2014 | Stone |
| 2014/0297310 A1 | 10/2014 | Collins, Jr. |
| 2014/0318699 A1 | 10/2014 | Longinotti-Buitoni et al. |
| 2014/0330147 A1 | 11/2014 | Ousdigian et al. |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0018660 A1 | 1/2015 | Thomson et al. |
| 2015/0022372 A1 | 1/2015 | Vosch |
| 2015/0048836 A1 | 2/2015 | Guthrie et al. |
| 2015/0065842 A1 | 3/2015 | Lee et al. |
| 2015/0087950 A1 | 3/2015 | Felix et al. |
| 2015/0094558 A1 | 4/2015 | Russell |
| 2015/0142090 A1 | 5/2015 | Duijsens et al. |
| 2015/0177175 A1 | 6/2015 | Elder et al. |
| 2015/0202351 A1 | 7/2015 | Kaplan et al. |
| 2015/0250422 A1 | 9/2015 | Bay |
| 2015/0257670 A1 | 9/2015 | Ortega et al. |
| 2015/0305676 A1 | 10/2015 | Shoshani |
| 2015/0335285 A1 | 11/2015 | Poon et al. |
| 2015/0359489 A1 | 12/2015 | Baudenbacher et al. |
| 2016/0029917 A1 | 2/2016 | Baker et al. |
| 2016/0135746 A1 | 5/2016 | Kumar et al. |
| 2016/0217691 A1 | 7/2016 | Kadobayashi et al. |
| 2018/0020931 A1 | 1/2018 | Shusterman |
| 2019/0021671 A1 | 1/2019 | Kumar et al. |
| 2019/0117068 A1 | 4/2019 | Thomson et al. |
| 2019/0223806 A1 | 7/2019 | Bennet et al. |
| 2021/0315504 A1 | 10/2021 | Kumar et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004121360 | 4/2004 |
| JP | 2004129788 | 4/2004 |
| JP | 2007082938 | 4/2007 |
| JP | 2009219554 | 10/2009 |
| WO | 9852463 | 11/1998 |
| WO | 0078213 | 12/2000 |
| WO | 0332192 | 4/2003 |
| WO | 0365926 | 8/2003 |
| WO | 2006009767 | 1/2006 |
| WO | 2006014806 | 2/2006 |
| WO | 2007066270 | 6/2007 |
| WO | 2007092543 | 8/2007 |
| WO | 2008005015 | 1/2008 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010104952 | 9/2010 |
| WO | 2010105045 | 9/2010 |
| WO | 2011047207 | 4/2011 |
| WO | 2012040487 | 3/2012 |
| WO | 2012112407 | 8/2012 |
| WO | 2012140559 | 10/2012 |
| WO | 2012146957 | 11/2012 |

OTHER PUBLICATIONS

"23 Personal Tools to Learn More About Yourself," Flowingdata.com, Sep. 18, 2008, 18 pages.

15 of the Hottest Wearable Gadgets, URL <http:/lthehottestgadgets.com/2008/09/the-15-hottest-wearable-gadgets-001253> (Web page cached on Sep. 27, 2008).

Actigraphy/ Circadian Rhythm SOMNOwatch, URL <http://www.somnomedics.eu/news-eventspublications/•omnowatchtm_html> (Web page cached on Jan. 23, 2010).

Adams et al., U.S. Appl. No. 61/755,623, filed Jan. 23, 2013, 48 pages.

Adinstruments:ECG Analysis Module for LabChart & Powerlab, 2008.

Alivecor, URL <http://www.businesswire.com/news/home/20121203005545/en/AliveCor%E2%80%99s-Heart-Monitor-Phone-Receives-FDA-Clearance#.U7rtq7FVTyF> (Dec. 3, 2012).

Alzaidi et al., "Smart Textiles Based Wireless ECG System," May 2012; 5 pages.

Anand et al., "Design of the Multi-Sensor Monitoring in Congestive Heart Failure (MUSIC) Study: Prospective Trial to Assess the Utility of Continuous Wireless Physiologic Monitoring in Heart Failure", Journal of Cardiac Failure (2011), 17(1), pp. 11-16.

Anonymous "Omegawave Launches Consumer App 2.0 in U.S. Endurance Sportswire—Endurance Sportswire." Jul. 11, 2013. URL:http://endurancesportswire_com/omegawave-launches-consumer-app-2-0-in-u-s/.

Au-Yeung et al., U.S. Appl. No. 60/765,467, filed Feb. 6, 2006, 25 pages.

Aventyn, Inc., "Vital Connect, Aventyn Launch Wearable Biosensor Platform for Mobile Patient Monitoring", Dec. 12, 2013, 5 pages.

*Bardy Diagnostics, Inc.* v. *Vital Connect, Inc.*, Defendant's Identification of Supplemental Prior Art References, C.A. No. 22-351 (CJV), May 22, 2024.

*Bardy Diagnostics, Inc.*, Plaintiff v. *Vital Connect, Inc.*; The United States District Court for the District of Delaware; C.A. No. 22-351 (CJB); Vitalconnect's Preliminary Invalidity Contentions; filed Oct. 25, 2023.

Bharadwaj et al., Techniques for Accurate ECG signal processing, EE Times, URL <www.eetimes.com/document.asp?doc_id=1278571> (Feb. 14, 2011 ).

BIOPAC Systems, Inc. #AS148-Automated ECG Analysis, Mar. 24, 2006.

Cesario et al., "Arrhythmia Detection with a Low-Profile Wireless

(56) References Cited

OTHER PUBLICATIONS

Adherent Cardiac Monitor: Results from the ADAM and EVE Studies", The Journal of Innovations in Cardiac Rhythm Management (2011), pp. 476-482.
Chaimanonart et al., "A Wireless Batteryless in vivo EKG and Body Temperature Sensing Microsystem with Adaptive RF Powering for Genetically Engineered Mice Monitoring," Jul. 2009; 4 pages.
Chan et al., "Wireless Patch Sensor for Remote Monitoring of Heart Rate, Respiration, Activity, and Falls." 2013 35th Annual International Conference of the IEEE Engineering in Medical and Biology Society, pp. 6115-6118.
Chart A-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar"); Oct. 25, 2023; 19 pages.
Chart A-2 Invalidity Contentions: U.S. Pat. No. 11,051,743; Case No. 22-351-CJB (Delaware); Invalidity of U.S. Pat. No. 11,051,743 by U.S. Pat. No. 11,116,447 ("Yang"); Oct. 25, 2023; 19 pages.
Chart A-3 Invalidity Contentions: U.S. Pat. No. 11,051,743; Case No. 22-351-CJB (Delaware); Invalidity of U.S. Pat. No. 11,051,743 by U.S. Pat. No. 10,327,660 ("Gallego"); Oct. 25, 2023; 12 pages.
Chart A-3 Invalidity Contentions: U.S. Pat. No. 11,445,967; Case No. 22-351-CJB (Delaware); Invalidity of U.S. Pat. No. 11,445,967 by U.S. Pat. No. 10,327,660 ("Gallego"); Oct. 25, 2023; 7 pages.
Chart A-4 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster"); Oct. 25, 2023; 11 pages.
Chart A-4 Invalidity Contentions: U.S. Pat. No. 11,445,967; Case No. 22-351-CJB (Delaware); Invalidity of U.S. Pat. No. 11,445,967 by U.S. Pat. Pub. No. 2011/0077497 ("Oster"); Oct. 25, 2023; 6 pages.
Chart A-5 Invalidity Contentions: U.S. Pat. No. 11,051,743; Case No. 22-351-CJB (Delaware); Invalidity of U.S. Pat. No. 11,051,743 by U.S. Pat. No. 10,413,251 ("Golda"); Oct. 25, 2023; 11 pages.
Chart A-6 Invalidity Contentions: U.S. Pat. No. 11,051,743; Case No. 22-351-CJB (Delaware); Invalidity of U.S. Pat. No. 11,051,743 by U.S. Pat. No. 9,669,212 ("Mueller"); Oct. 25, 2023; 11 pages.
Chart A-7 Invalidity Contentions: U.S. Pat. No. 11,051,743; Case No. 22-351-CJB (Delaware); Invalidity of U.S. Pat. No. 11,051,743 by U.S. Pat. No. 7,206,630 ("Tarler"); Oct. 25, 2023; 12 pages.
Chart A-8 Invalidity Contentions: U.S. Pat. No. 11,051,743; Case No. 22-351-CJB (Delaware); Invalidity of U.S. Pat. No. 11,051,743 by WO 2008/005015 ("Shennib"); Oct. 25, 2023; 12 pages.
Chart A-9 Invalidity Contentions: U.S. Pat. No. 11,051,743; Case No. 22-351-CJB (Delaware); Invalidity of U.S. Pat. No. 11,051,743 by U.S. Pat. Pub. No. 2011/0009729 ("Shin"); Oct. 25, 2023; 12 pages.
Chart A-10 Invalidity Contentions: U.S. Pat. No. 11,051,743; Case No. 22-351-CJB (Delaware); Invalidity of U.S. Pat. No. 11,051,743 by WO 2003/065926 ("Ozguz"); Oct. 25, 2023; 12 pages.
Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar") and U.S. Pat. No. 11,116,447 ("Yang"); Oct. 25, 2023; 24 pages.
Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar"); Oct. 25, 2023; 13 pages.
Chart AA-2 Invalidity Contentions: U.S. Pat. No. 11,445,967; Case No. 22-351-CJB (Delaware); Invalidity of U.S. Pat. No. 11,445,967 by U.S. Patent No. 11, 116,447 ("Yang"); Oct. 25, 2023; 14 pages.
Chart AA-5 Invalidity Contentions: U.S. Pat. No. 11,445,967; Case No. 22-351-CJB (Delaware); Invalidity of U.S. Pat. No. 11,445,967 by U.S. Pat. No. 10,413,251 ("Golda"); Oct. 25, 2023; 6 pages.
Chart AA-6 Invalidity Contentions: U.S. Pat. No. 11,445,967; Case No. 22-351-CJB (Delaware); Invalidity of U.S. Pat. No. 11,445,967 by U.S. Pat. No. 9,669,212 ("Mueller"); Oct. 25, 2023; 6 pages.
Chart AA-7 Invalidity Contentions: U.S. Pat. No. 11,445,967; Case No. 22-351-CJB (Delaware); Invalidity of U.S. Pat. No. 11,445,967 by U.S. Pat. No. 7,206,630 ("Tarler"); Oct. 25, 2023; 7 pages.
Chart AA-8 Invalidity Contentions: U.S. Pat. No. 11,445,967; Case No. 22-351-CJB (Delaware); Invalidity of U.S. Pat. No. 11,445,967 by WO 2008/005015 ("Shennib"); Oct. 25, 2023; 6 pages.
Chart AA-9 Invalidity Contentions: U.S. Pat. No. 11,445,967; Case No. 22-351-CJB (Delaware); Invalidity of U.S. Pat. No. 11,445,967 by U.S. Pat. Pub. No. 2011/0009729 ("Shin"); Oct. 25, 2023; 6 pages.
Chart AA-10 Invalidity Contentions: U.S. Pat. No. 11,445,967; Case No. 22-351-CJB (Delaware); Invalidity of U.S. Pat. No. 11,445,967 by WO 2003/065926 ("Ozguz"); Oct. 25, 2023; 6 pages.
Chart B-1 Invalidity Contentions: U.S. Pat. No. 11,051,743 and U.S. Pat. No. 11,445,967; Case No. 22-351-CJB (Delaware); Elongated Strip With Narrowed Midsection; Oct. 25, 2023; 8 pages.
Chart B-2 Invalidity Contentions: U.S. Pat. No. 11,051,743 and U.S. Pat. No. 11,445,967; Case No. 22-351-CJB (Delaware); An Electrocardiogramactrode on Each End of the Backing; Oct. 25, 2023; 8 pages.
Chart B-3 Invalidity Contentions: U.S. Pat. No. 11,051,743 and U.S. Pat. No. 11,445,967; Case No. 22-351-CJB (Delaware); Flexible Circuit Comprising a Pair of Circuit Traces to Couple Electrodes; Oct. 25, 2023; 8 pages.
Chart B-4 Invalidity Contentions: U.S. Pat. No. 11,051,743 and U.S. Pat. No. 11,445,967; The Case No. 22-351- CJB (Delaware); Rounded Outer Edge of Backing Ends; Oct. 25, 2023; 5 pages.
Chart B-5 Invalidity Contentions: U.S. Pat. No. 11,051,743 and U.S. Pat. No. 11,445,967; Case No. 22-351-CJB (Delaware); Conversion of Electrocardiogramanals From One Format to Another; Oct. 25, 2023; 6 pages.
Chart B-6 Invalidity Contentions: U.S. Pat. No. 11,051,743 and U.S. Pat. No. 11,445,967; Case No. 22-351-CJB (Delaware); Hydrocolloid Adhesives on a Portion of the Backing; Oct. 25, 2023; 5 pages.
Chart B-7 Invalidity Contentions: U.S. Pat. No. 11,051,743 and U.S. Pat. No. 11,445,967; Case No. 22-351-CJB (Delaware); A Patch Comprising Adhered Layers; Oct. 25, 2023; 16 pages.
Chart C-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar") and U.S. Pat. No. 11,116,447 ("Yang"); Oct. 25, 2023; 32 pages.
[Corrected] Chart C-2 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster") and U.S. Pat. No. 11,116,447 ("Yang"); Oct. 25, 2023; 22 pages.
[CORRECTED] Chart CC-2 Invalidity Contentions: U.S. Pat. No. 11,445,967; Case No. 22-351-CJB (Delaware); Invalidity of U.S. Patent No. by U.S. Pat. Pub. No. 2011/0077497 ("Oster") and U.S. Pat. No. 11,116,447 ("Yang"); Oct. 25, 2023; 16 pages.
Chen et al. "Monitoring Body Temperature of Newborn Infants At Neonatal Intensive Care Units Using Wearable Sensors," BodyNets 2010, Corfu Island, Greece. Sep. 10-12, 1210.
Complaint from Case No. 1 :22-cv-00351-UNA, *Bardy Diagnostics, Inc.* (Plaintiff) v . *Vital Connect, Inc.* (Defendant), filed: Mar. 18, 2022, 182 pages.
Corventis Avivo, "Aviva Mobile Patient Management System", Corventis, 2008, lasted printed Jul. 18, 2024, https://web. archive. org/web/20100118155329/http://www.corventis.com/AP/avivo.Asp.
Corventis Nuvant, "Nuvant Mobile Cardiac Telementry (MTC) System", Corventis, 2009, last printed Jul. 18, 2024, https://web. archive.org/web/20100127193736/http:I/corventis. com/AP/nuvant. Asp.
Daoud et al. "Fall Detection Using Shimmer Technology And Multiresolution Analysis." Aug. 2, 2013. URL: https://decibel.ni.com/content/docs/DOC-26652.
Dec. 26, 2022 Letter from Opposing Counsel, 1:22-cv-00351-CJB; *Bardy Diagnostics, Inc.* v_ *Vital Connect, Inc.* D. Del.); and IPR2023-00381; *Vital Connect, Inc.* v. *Bardy Diagnostics, Inc.* (P.T.A.B.), Dec. 26, 2022.
Defendant's Answer, Defenses, and Counterclaim from Case. No. 1:22-cv-00351-CFC, *Bardy Diagnostics, Inc.* (Plaintiff) v. *Vital Connect, Inc.* (Defendant), Filed May 25, 2022, 132 pages.

(56) References Cited

OTHER PUBLICATIONS

Defendant's Opening Brief in Support of Its Motion to Dismiss For Failure to State A Claim from Case No. 1:22-"v.00351-CFC, *Bardy Diagnostics, Inc.* (Plaintiff) v. *Vital Connect, Inc.* (Defendant), Filed: May 25, 2022, 18 pages.
Defendant's Reply Brief In Support of Its Motion to Dismiss For Failure to State a Claim from Case No. 1 :22-cv-00351-CFC, *Bardy Diagnostics, Inc.* (Plaintiff) v. *Vital Connect, Inc.* (Defendant), Filed: Jun. 15, 2022, 93 pages.
Duttweiler et al., "Probability Estimation in Arithmetic and Adaptive-Huffman Entropy Coders," IEEE Transactions in Image Processing_ vol. 4, No. 3, Mar. 1, 1995, pp. 237-246.
Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.
First Amended Complaint for Patent Infringement, 1:22-cv-00351-CJB, *Bardy Diagnostics, Inc_* v. *Vital Connect, Inc.* D. Del.), filed Jan. 10, 2023.
First Examination Report, Communication pursuant to Article 94(3) EPC, 19 828 053.9-1113, dated Apr. 15, 2024.
Fitbit Tracker, URL <http://www.fitbit.com/> (Web page cached on Sep. 10, 2008.).
Gravitz, Lauren, "When Your Diet Needs A Band-Aid, "Technology Review, MIT. (May 1, 2009).
Gupta et al., "An ECG Compression Technique for Telecardiology Application," India Conference (INDICON), 2011 Annual IEEE, Dec. 16, 2011, pp. 1-4.
Harland et al., "Electric Potential Probes-New Directions in the Remote Sensing of the Human Body", Measurement Science and Technology (2002), vol. 13, pp. 163-169.
Hill, "Adventures in Self-Surveillance: Fitbit, Tracking My Movement and Sleep," Forbes, Feb. 25, 2011, 11 pages.
http://www.gtec.at/Products/Software/g. BSanalyze-Specs-Features (2014 ).
http://www.originlab.com/origin#Data_Exploration 2015.
https://fccid.io/LF524950/User-Manual/User-Manual-1944573 © Medtronic, Inc. 2012.
https://web.archive.org/web/20130831204020/http:/lwww .biopac.com/research .asp?Catl 0=37 &Main=Software (Aug. 2013).
Initial hands-on with sirdv activity tracker, URL <http://www.dcrainmaker.com/2013/09/polar-loop-firstlook.html> Sep. 17, 2013).
International Preliminary Report on Patentability and Written Opinion, PCT/US2019/064331, Jun. 8, 2021.
Invalidity of U.S. Pat. No. 11,051,743 by U.S. Pat. Pub. No. 2011/0077497 ("Oster"); Oct. 25, 2023; 11 pages.
iRhythm ZIO XT Patch/Event Card, "Zio Patch", iRhythm, 2011, last printed Jul. 18, 2024, https://web.archive.org/web/20111017074139/http://irhythmtech.com/media/files/Z1 00A4020.04%20-%20ZIO%20PATCH%20DATA%20SHEET.pdf.
*iRhythm, Inc*.v. *Welch Allyn, Inc.*, Expert Declaration of Jason Heikenfeld for U.S. Pat. Nos. 8,214,007, 8,965,492, 9,155,484, and 10,159,422 dated Dec. 20, 2024. 516 pages.
*iRhythm, Inc*.v. *Welch Allyn, Inc.*, Petition for Inter Partes Review Under 35 U.S.C. § 312 AND 37 C.F.R. § 42.104, Case No. IPR2025-00363 for U.S. Patent No. 10, 159,422, dated Dec. 23, 2024. 94 pages.
*iRhythm, Inc*.v. *Welch Allyn, Inc.*, Petition for Inter Partes Review Under 35 U.S.C. § 312 AND 37 C.F.R. § 42.104, Case No. IPR2025-00374 for U.S. Pat. No. 8,965,492, dated Dec. 23, 2024. 86 pages.
*iRhythm, Inc*.v. *Welch Allyn, Inc.*, Petition for Inter Partes Review Under 35 U.S.C. § 312 AND 37 C.F.R. § 42.104, Case No. IPR2025-00376 for U.S. Pat. No. 9,155,484, dated Dec. 23, 2024. 106 pages.
*iRhythm, Inc*.v. *Welch Allyn, Inc.*, Petition for Inter Partes Review Under 35 U.S.C. § 312 AND 37 C.F.R. § 42.104, Case No. IPR2025-00377 for U.S. Pat. No. 8,214,007, dated Dec. 23, 2024. 88 pages.

*iRhythm, Inc*.v. *Welch Allyn, Inc.*, Petition for Inter Partes Review Under 35 U.S.C. § 312 AND 37 C.F.R. § 42.104, Case No. IPR2025-00378 for U.S. Pat. No. 8,214,007, dated Dec. 23, 2024. 95 pages.
Ivanov, G.G., "HRV Analysis Under the Usage of Different Electrocardiopraphy Systems," Apr. 15, 2008, (Apr. 15, 2008), XP55511209, Retrieved from the Internet: URL:http://www.drkucera.eu/upload_doc/ hrv_analysis_methodical_recommendations)_pdf [retrieved on Oct. 1, 2018].
Kligfield, Paul et al., Recommendations for the Standardization and Interpretation of the Electrocardiogram: Part I. U. Am.Coll. Cardiol; 2007; 49; 1109-27, 75 Pgs.
Knight et al., U.S. Appl. No. 60/786,502, filed Mar. 29, 2006, 8 pages.
Leonard, Dwayne C., "A Framework for the Creation of a Unified Electronic Medical Record Using Biometrics", Data Fusion and Belief Theory (2007), <https://dialong.proquest.com/professional/docview/304852676/17AEEF1F9382EF1C4E5/6?accountid=131444> (last visited Aug. 27, 2021).
Libbus, "Adherent Cardiac Monitor With Wireless Fall Detection for Patients With Unexplained Syncope." Abstracts t>f the First AMA-IEEE Medical Technology Conference on Individualized Healthcare. May 22, 2010.
Lieberman, Jonathan "How Telemedicine Is Aiding Prompt ECG Diagnosis in Primary Care," British Journal of Community Nursing, vol. 13, No. 3, Mar. 1, 2008, pp. 123-126, XP009155082, ISSN: 1462-4753.
May 2, 2022 Letter From Counsel. 1:22-cv-00351-CFC. May 2, 2022.
May 24, 2022 Letter to Opposing Counsel. 1:22-cv-00351-CFC. May 24, 2022.
McManus et al., "A Novel Application for the Detection of an Irregular Pulse using an iphone 4S in Patients with Atrial Fibrillation," vol. 10(3), pp. 315-319 (Mar. 2013.).
Mehen, "Open health with the quantified self," Opensource.com, Aug. 25, 2011, 7 pages.
Mukala et al., "A Novel Zigbee- based Low- cost, Low- Power Wireless EKG system," IEEE, May 2010; 4 pages.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Nike+ Fuel Band, URL <http://www.nike.com/us/en_us/c/nikeplus-fuelband> (Web page cached on Jan. 11, 2013.).
Nov. 11, 2022, Letter from Opposing Counsel, 1 :22-cv-00351-CJB; *Bardy Diagnostics, Inc.* v_ *Vital Connect, Inc.* D.Del.), Nov. 11, 2022.
Oct. 17, 2022 Letter to Opposing Counsel, *Bardy Diagnostics, Inc_* v_ *Vital Connect, Inc.*, No. 22-cv-00351-CFC D. Del.), Oct. 17, 2022.
P. Libby et al., "Braunwald's Heart Disease—A Textbook of Cardiovascular Medicine," Chs_ 11, pp. 125-148 and 12, pp. 149-193 (8th ed_ 2008), American Heart Association.
Pandian et al., "Wireless Sensor Network for Wearable Physiological Monitoring," Journal of Networks, vol. 3, No. 5, May 2008; 15 pages.
Petition for Inter Partes Review of U.S. Pat. No. 11,051,743 Pursuant to 35 U.S.C. §§ 311-319 and 37 C.F.R. § 42, Case No. IPR2023-00381, *Vital Connect, Inc.* v. *Bardy Diagnostics, Inc.* (P.T.A.B.), Dec. 21, 2022, 875 pages.
Plaintiff's Answer Brief in Opposition to Defendant's Motion to Dismiss for Failure to State a Claim from Case No. 1:22-cv-00351-CFC, *Bardy Diagnostics, Inc.* (Plaintiff) v. *Vital Connect, Inc.* (Defendant), Filed Jun. 8, 2022, 25 pages.
Plaintiffs Answer to Defendant's Counterclaim from Case No. 1 :22-cv-00351-CFC, *Bardy Diagnostics, Inc.* (Plaintiff) v. *Vital Connect, Inc.* (Defendant), Filed: Jun. 15, 2022, 5 pages.
Puurtinen et al., "Estimation of ECG Signal of closely separated bipolar electrodes using thorax models," Proceedings of the 26th Annual International Conference of the IEEE EMBS pp. 801-804, San Francisco, Calif., USA, Sep. 1-5, 2004, 4 pages.
Saadi et al. "Heart Rhythm Analysis Using ECG Recorded With a Novel Sternum Based Patch Technology—A Pilot Study_" Cardio

(56) References Cited

OTHER PUBLICATIONS technix 2013—Proceedings of the International Congress on Cardiovascular Technologies, Sep. 20, 2013.
Saeed et al., "A Scalable Wireless Body Area Sensor Network for Health-Care Monitoring," Jun. 2009, 4 pages.
Sapoznikov, Dan et al., "Comparison of Different Methodologies of Heart Rate Variability Analysis," Department of Cardiology, Hadassah University Hospital, P.O.B. 12000, Ein Kerem, Jerusalem 91120, Israel (1993).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Skretting et al., "Improved Huffman Coding Using Recursive Splitting," NORSIG, Jan. 1, 1999.
Sleepview, URL <http://www.clevemed.com/sleepview/overview.shtml> (Web page cached on Sep. 4, 2013.).
Smith, Jawbone Up, URL <http://www.businessinsider.com/fitbit-flex-vs-jawbone-up-2013-5?op=1> (Jun. 1, 2013).
Toth et al., U.S. Appl. No. 61/832,131, filed Jun. 6, 2013, 82 pages.
Trägårdh et al., How Many ECG Leads Do We Need? Cardiology Clinics. Aug. 2006; 24(3): 317-30, vii. doi: 10.1016/j.ccl.2006.04.005. PMID: 16939826; 14 pages.
Varicrad-Kardi Software User's Manual Rev_ 1.1, Jul. 8, 2009 (Jul. 8, 2009), XP002757888, retrieved from the Internet: URL:http://www.ehrlich.tv/KARDiVAR-Software.pdf [retrieved on May 20, 2016].
Vishnubhotla, "Pre-processing of ECG signals for ambulatory use," Jan. 2009; 5 pages.
Voss, A. et al., "Linear and Nonlinear Methods for Analyses of Cardiovascular Variability in Bipolar Disorders," Bipolar Disorders, vol. 8, No. 5 p1, Oct. 1, 2006, pp. 441-452, XP55273826, DK ISSN: 1398-5647, DOI: 10.1111/.1399-5618 -2006 .00364 x.
Wallot et al., "Using Complexity Metrics With R-R Intervals and BPM Heart Rate Measures," Frontiers in Physiology, vol. 4, Article 211, pp. 1-8, Aug. 13, 2013. 2013.
Wolf, "The Data-Driven Life," New York Times Magazine, Apr. 28, 2010, 13 pages.
Zio Event Card, URL <http://www.irhythmtech.com/zio-solution/zio-event/> (Web page cached on Mar. 11, 2013.).
Zio Patch System, URL <http://www.irhythmtech.com/zio-solution/zio-system/index.html> (Web page cached on Sep. 8, 2013.).
*Bardy Diagnostics, Inc.*, Plaintiff v. *Irhythm Technologies, Inc.*; The United States District Court for the District of Delaware; Complaint against iRhythm Technologies; filed Dec. 10, 2024.
Exhibits 1-13 for *Bardy Diagnostics, Inc.*, Plaintiff v. *Irhythm Technologies, Inc.*; The United States District Court for the District of Delaware; Complaint against iRhythm Technologies; filed Dec. 10, 2024.
*Bardy Diagnostics, Inc.*, Plaintiff v. *Irhythm Technologies, Inc.*; The United States District Court for the District of Delaware; C.A. No. 24-1355-RGA; First Amended Complaint against iRhythm Technologies; filed Dec. 26, 2024.
Exhibits 1-15 for *Bardy Diagnostics, Inc.*, Plaintiff v. *Irhythm Technologies, Inc.*; The United States District Court for the District of Delaware; C.A. No. 24-1355-RGA; First Amended Complaint against iRhythm Technologies; filed Dec. 26, 2024.
*Bardy Diagnostics, Inc.*, Plaintiff v. *Irhythm Technologies, Inc.*; The United States District Court for the District of Delaware; C.A. No. 24-1355 (JDW); Defendant iRhythm Technologies, Inc.'s Counterclaim and Answer to Plaintiff Bardy Diagnostics, Inc.'s First Amended Complaint; filed Mar. 3, 2025.
Exhibits 1-10 for *Bardy Diagnostics, Inc.*, Plaintiff v. *Irhythm Technologies, Inc.*; The United States District Court for the District of Delaware; C.A. No. 24-1355 (JDW); Defendant iRhythm Technologies, Inc.'s Counterclaim and Answer to Plaintiff Bardy Diagnostics, Inc.'s First Amended Complaint; filed Mar. 3, 2025.
*Vital Connect, Inc.* v. *Bardy Diagnostics, Inc.*, USPTO Patent Trial & Appeal Board - Patent Owner's Preliminary Response, Case No. IPR2023-00381 for U.S. Pat. No. 11,051,743, dated Apr. 24, 2023. 53 pages.
*Vital Connect, Inc.* v. *Bardy Diagnostics, Inc.*, USPTO Patent Trial & Appeal Board - DECISION Denying Institution of Inter Partes Review 35 U.S.C. § 314, Case No. IPR2023-00381 for U.S. Pat. No. 11,051,743, dated Jul. 11, 2023. 21 pages.
*Vital Connect, Inc.* v. *Bardy Diagnostics, Inc.*, USPTO Patent Trial & Appeal Board—Order, Case No. IPR2023-00381 for U.S. Pat. No. 11,051,743, dated Oct. 3, 2023. 3 pages.
*Vital Connect, Inc.* v. *Bardy Diagnostics, Inc.*, USPTO Patent Trial & Appeal Board—Declaration of Dr. Per Reinhall, Ph.D, Case No. IPR2023-00381 for U.S. Pat. No. 11,051,743, dated Apr. 21, 2023. 28 pages.
Bardy Diagnostics Statutory Disclaimer Under 35 U.S.C. 253(a) and 37 C.F.R. § 1.321(a) for U.S. Pat. No. 11,051,743, dated Apr. 21, 2023. 2 pages.
Defendant's Answer to First Amended Complaint, Defenses, and Counterclaim, 1 :22-cv-00351-CJB, *BardyDiagnostics, Inc.* v. *Vital Connect, Inc.* (D. Del.), filed Jan. 24, 2023 (227 pages).
Non-Final Office Action from U.S. Appl. No. 18/933,792, mailed Mar. 20, 2025. 27 pages.
*iRhythm, Inc.* v. *Welch Allyn, Inc.*, Petition for Inter Partes Review Under 35 U.S.C. § 312 AND 37 C.F.R. § 42.104, Case No. IPR2025-01081 for U.S. Pat. No. 8,630,699, dated Jun. 3, 2025. 81 pages.

EXTENDED WEAR AMBULATORY ELECTROCARDIOGRAMAY MONITOR

PRIORITY CLAIM AND CROSS-REFERENCE TO RELATED APPLICATIONS

This application is a continuation of U.S. patent application Ser. No. 18/353,407, filed Jul. 17, 2023, titled EXTENDED WEAR AMBULATORY ELECTROCARDIOGRAPHY MONITOR, which is a continuation application of U.S. patent Ser. No. 17/691,004, filed Mar. 9, 2022, titled EXTENDED WEAR AMBULATORY ELECTROCARDIOGRAPHY MONITOR, which is a continuation of U.S. patent application Ser. No. 16/684,386, filed Nov. 14, 2019, titled EXPENDED WEAR AMBULATORY ELECTROCARDIOGRAPHY AND PHYSIOLOGICAL SENSOR MONITOR, which is a continuation of U.S. patent application Ser. No. 15/676,896, filed Aug. 14, 2017, titled EXTENDED WEAR AMBULATORY ELECTROCARDIOGRAPHY AND PHYSIOLOGICAL SENSOR MONITOR, which is a continuation of U.S. patent application Ser. No. 14/080,725, filed Nov. 14, 2013, titled EXTENDED WEAR AMBULATORY ELECTROCARDIOGRAPHY AND PHYSIOLOGICAL SENSOR MONITOR, which claims priority to U.S. Provisional Patent App. No. 61/882,403, filed Sep. 25, 2013, titled LONG-TERM WEARABLE PHYSIOLOGICAL MONITOR. The entire contents of these applications are incorporated by reference herein in their entirely and relied upon.

FIELD

This application relates in general to electrocardiographic monitoring and, in particular, to an extended wear ambulatory electrocardiography monitor.

BACKGROUND

The heart emits electrical signals as a by-product of the propagation of the action potentials that trigger depolarization of heart fibers. An electrocardiogram (ECG) measures and records such electrical potentials to visually depict the electrical activity of the heart over time. Conventionally, a standardized set format 12-lead configuration is used by an ECG machine to record cardiac electrical signals from well-established traditional chest locations. Electrodes at the end of each lead are placed on the skin over the anterior thoracic region of the patient's body to the lower right and to the lower left of the sternum, on the left anterior chest, and on the limbs. Sensed cardiac electrical activity is represented by PQRSTU waveforms that can be interpreted post-ECG recordation to derive heart rate and physiology. The P-wave represents atrial electrical activity. The QRSTU components represent ventricular electrical activity.

An ECG is a tool used by physicians to diagnose heart problems and other potential health concerns. An ECG is a snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease. ECGs are used in-clinic during appointments, and, as a result, are limited to recording only those heart-related aspects present at the time of recording. Sporadic conditions that may not show up during a spot ECG recording require other means to diagnose them. These disorders include fainting or syncope; rhythm disorders, such as tachyarrhythmias and bradyarrhythmias; apneic episodes; and other cardiac and related disorders. Thus, an ECG only provides a partial picture and can be insufficient for complete patient diagnosis of many cardiac disorders.

Diagnostic efficacy can be improved, when appropriate, through the use of long-term extended ECG monitoring. Recording sufficient ECG and related physiology over an extended period is challenging, and often essential to enabling a physician to identify events of potential concern. A 30-day observation day period is considered the "gold standard" of ECG monitoring, yet achieving a 30-day observation day period has proven unworkable because such ECG monitoring systems are arduous to employ, cumbersome to the patient, and excessively costly. Ambulatory monitoring in-clinic is implausible and impracticable. Nevertheless, if a patient's ECG could be recorded in an ambulatory setting, thereby allowing the patient to engage in activities of daily living, the chances of acquiring meaningful information and capturing an abnormal event while the patient is engaged in normal activities becomes more likely to be achieved.

For instance, the long-term wear of ECG electrodes is complicated by skin irritation and the inability ECG electrodes to maintain continual skin contact after a day or two. Moreover, time, dirt, moisture, and other environmental contaminants, as well as perspiration, skin oil, and dead skin cells from the patient's body, can get between an ECG electrode, the non-conductive adhesive used to adhere the ECG electrode, and the skin's surface. All of these factors adversely affect electrode adhesion and the quality of cardiac signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Notwithstanding the cause of electrode dislodgment, depending upon the type of ECG monitor employed, precise re-placement of a dislodged ECG electrode maybe essential to ensuring signal capture at the same fidelity. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

Conventionally, Holter monitors are widely used for long-term extended ECG monitoring. Typically, they are often used for only 24-48 hours. A typical Holter monitor is a wearable and portable version of an ECG that include cables for each electrode placed on the skin and a separate battery-powered ECG recorder. The cable and electrode combination (or leads) are placed in the anterior thoracic region in a manner similar to what is done with an in-clinic standard ECG machine. The duration of a Holter monitoring recording depends on the sensing and storage capabilities of the monitor, as well as battery life. A "looping" Holter monitor (or event) can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest hinders or precludes a patient from replacing or removing the precordial leads and usually involves moving the patient from the physician office to a specialized center within the hospital or clinic.

The ZIO XT Patch and ZIO Event Card devices, manufactured by iRhythm Tech., Inc., San Francisco, CA, are wearable stick-on monitoring devices that are typically worn on the upper left pectoral region to respectively provide continuous and looping ECG recording. The location is used to simulate surgically implanted monitors. Both of these devices are prescription-only and for single patient use. The ZIO XT Patch device is limited to a 14-day monitoring period, while the electrodes only of the ZIO Event Card device can be worn for up to 30 days. The ZIO XT Patch device combines both electronic recordation components, including battery, and physical electrodes into a unitary assembly that adheres to the patient's skin. The ZIO XT Patch device uses adhesive sufficiently strong to support the weight of both the monitor and the electrodes over an extended period of time and to resist disadherance from the patient's body, albeit at the cost of disallowing removal or relocation during the monitoring period. Moreover, throughout monitoring, the battery is continually depleted and battery capacity can potentially limit overall monitoring duration. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of atrial (P-wave) signals.

Therefore, a need remains for an extended wear continuously recording ECG monitor practicably capable of being worn for a long period of time in both men and women and capable of recording atrial signals reliably.

A further need remains for a device capable of recording signals ideal for arrhythmia discrimination, especially a device designed for atrial activity recording.

SUMMARY

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, benefits long-term extended wear by removing the requirement that ECG electrodes be continually placed in the same spots on the skin throughout the monitoring period. Instead, the patient is free to place an electrode patch anywhere within the general region of the sternum. In addition, power is provided through a battery provided on the electrode patch, which avoids having to either periodically open the housing of the monitor recorder for the battery replacement, which also creates the potential for moisture intrusion and human error, or to recharge the battery, which can potentially take the monitor recorder off line for hours at a time. In addition, the electrode patch is intended to be disposable, while the monitor recorder is a reusable component. Thus, each time that the electrode patch is replaced, a fresh battery is provided for the use of the monitor recorder.

One embodiment provides an extended wear electrocardiography and physiological sensor monitor recorder that includes a sealed housing configured to be removably secured into a receptacle on an electrode patch that has a battery electrically interfaced to a pair of electrical pads on the receptacle. The sealed housing also includes a set of electrical contacts that protrude from a bottom surface and correspond with further electrical pads on the receptacle. Electronic circuitry is provided within the sealed housing and includes a micro-controller operable to execute under micro-programmable control, an electrographic front end circuit electrically interfaced to the micro-controller and operable to sense electrocardiographic signals through electrocardiographic electrodes provided on the electrode patch, and a flash memory electrically interfaced with the micro-controller and operable to store samples of the electrocardiographic signals.

A further embodiment provides an electrocardiography monitor. A sealed housing includes one end wider than an opposite end of the sealed housing. Electronic circuitry is provided within the sealed housing. The electronic circuitry includes an electrographic front end circuit to sense electrocardiographic signals and a micro-controller interfaced to the electrocardiographic front end circuit to sample the electrocardiographic signals. A buzzer within the housing outputs feedback to a wearer of the sealed housing.

A still further embodiment provides an extended wear electrocardiography and physiological sensor monitor that includes an electrode patch having a flexible backing formed of an elongated strip and a pair of electrocardiographic electrodes conductively exposed on a contact surface of each end of the elongated strip. A receptacle is adhered to an outward-facing side of the elongated strip opposite the contact surface and includes a plurality of electrical pads. A battery is electrically interfaced to a pair of the electrical pads on the receptacle. A flexible circuit is affixed on each end of the elongated strip and includes a pair of circuit traces electrically coupled to the pair of electrocardiographic electrodes and another pair of the electrical pads. An electrocardiography monitor includes a sealed housing configured to be removably secured into the receptacle on the electrode patch and has a set of electrical contacts that protrude from a bottom surface and correspond with further electrical pads on the receptacle. Electronic circuitry is provided within the sealed housing and includes a micro-controller operable to execute under micro-programmable control, an electrographic front end circuit electrically interfaced to the micro-controller and operable to sense electrocardiographic signals through the electrocardiographic electrodes provided on the electrode patch, and a flash memory electrically interfaced with the micro-controller and operable to store samples of the electrocardiographic signals.

The monitoring patch is especially suited to the female anatomy. The narrow longitudinal midsection can fit nicely within the intermammary cleft of the breasts without inducing discomfort, whereas conventional patch electrodes are wide and, if adhesed between the breasts, would cause chafing, irritation, frustration, and annoyance, leading to low patient compliance.

The foregoing aspects enhance ECG monitoring performance and quality facilitating long-term ECG recording, critical to accurate arrhythmia diagnosis.

In addition, the foregoing aspects enhance comfort in women (and certain men), but not irritation of the breasts, by placing the monitoring patch in the best location possible for optimizing the recording of cardiac signals from the atrium, another feature critical to proper arrhythmia diagnosis.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
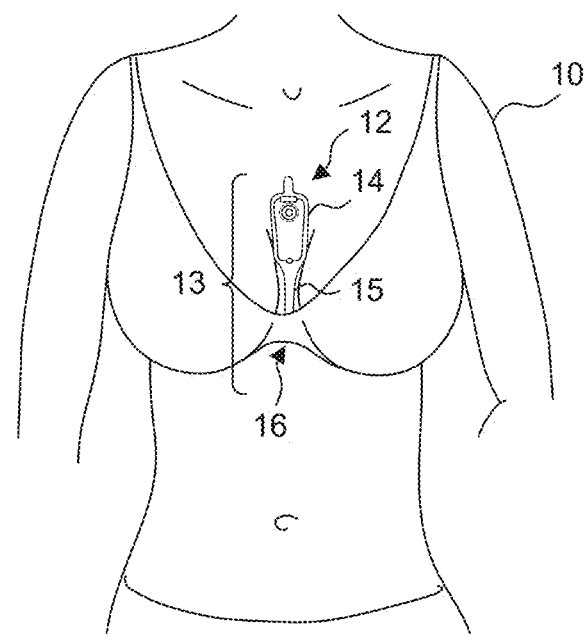
FIGS. 1 and 2 are diagrams showing, by way of examples, an extended wear electrocardiography and physiological sensor monitor, including a monitor recorder in accordance with one embodiment, respectively fitted to the sternal region of a female patient and a male patient.
Figure 2:
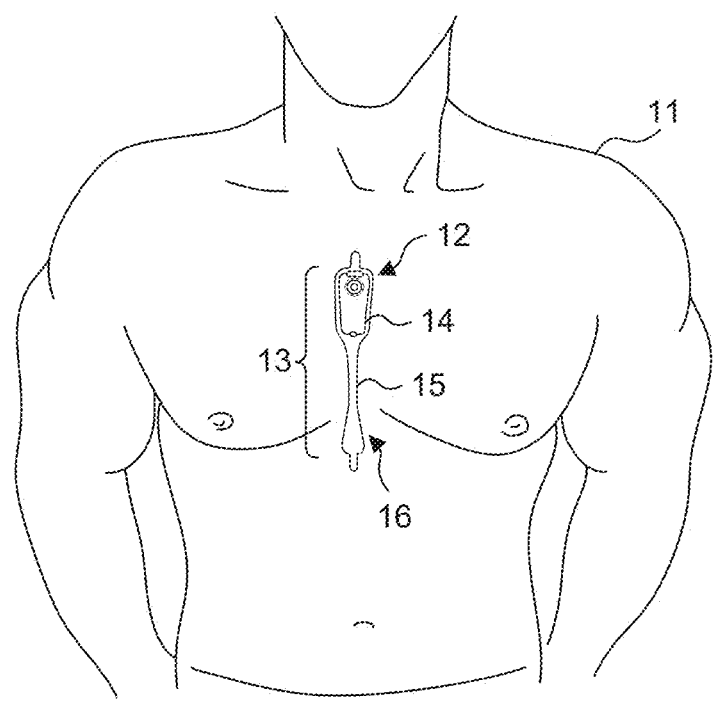

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography and physiological sensor monitor 12, including a monitor recorder 14 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. In a further embodiment, the orientation of the wearable monitor 12 can be corrected post-monitoring, as further described infra. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region. In addition, placing the lower or inferior pole (ECG electrode) of the electrode patch 15 over (or near) the Xiphoid process facilitates sensing of right ventricular activity and provides superior recordation of the QRS interval.

Figure 3:
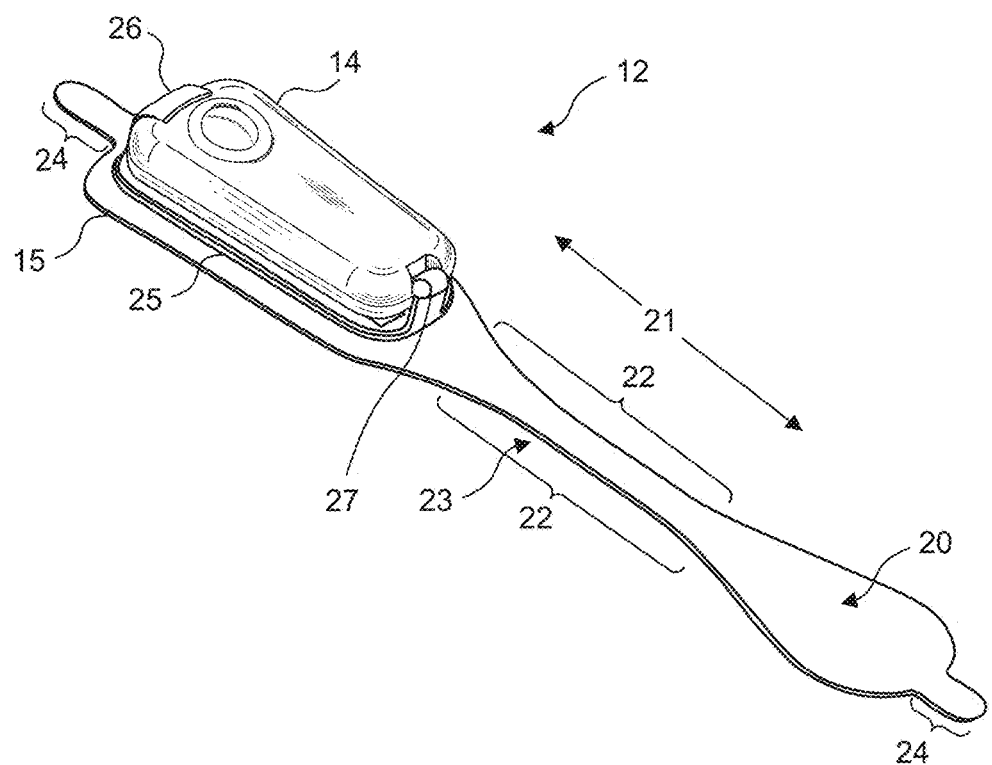
FIG. 3 is a perspective view showing an extended wear electrode patch with a monitor recorder in accordance with one embodiment inserted.

During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 3 is a perspective view showing an extended wear electrode patch 15 with a monitor recorder 14 in accordance with one embodiment inserted. The body of the electrode patch 15 is preferably constructed using a flexible backing 20 formed as an elongated strip 21 of wrap knit or similar stretchable material with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above.

The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates strain and crimp reliefs, such as described in commonly-assigned U.S. Patent, entitled "Extended Wear Electrocardiography Patch," U.S. Pat. No. 9,545,204, issued on Jan. 17, 2017, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, as further described infra beginning with reference to FIG. 8. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 4:
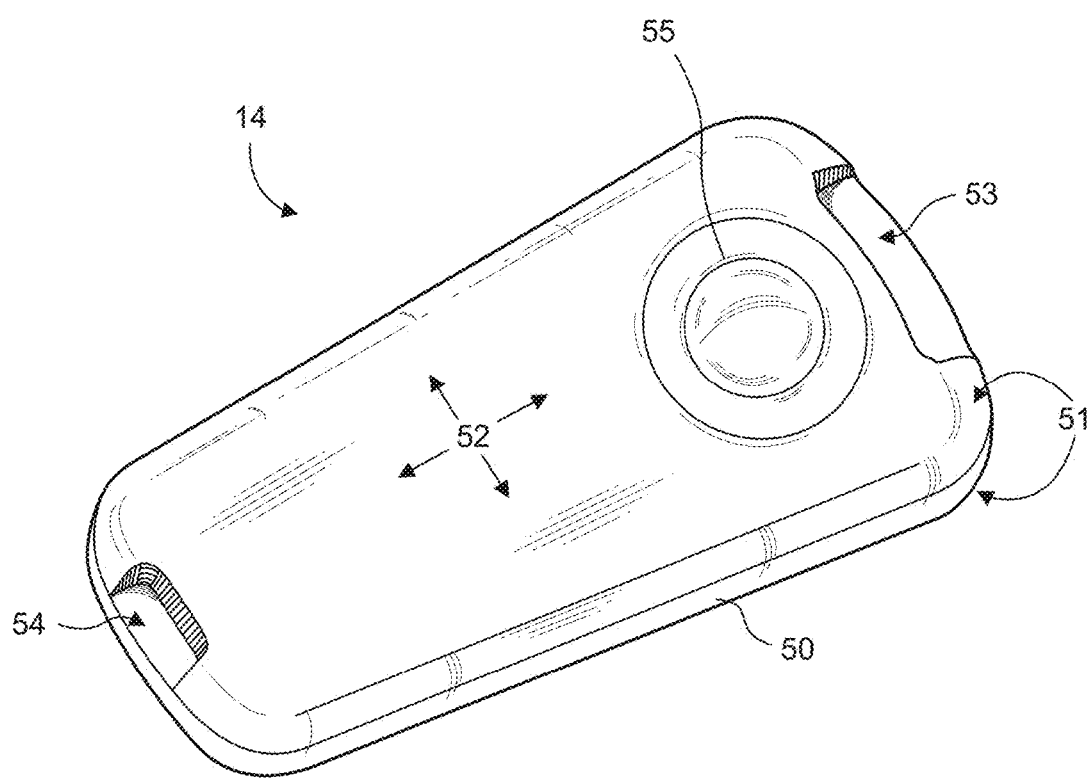
FIG. 4 is a perspective view showing the monitor recorder of FIG. 3.

The monitor recorder 14 includes a sealed housing that snaps into place in the non-conductive receptacle 25. FIG. 4 is a perspective view showing the monitor recorder 14 of FIG. 3. The sealed housing 50 of the monitor recorder 14 intentionally has a rounded isosceles trapezoidal-like shape 52, when viewed from above, such as described in commonly-assigned U.S. Design Patent, entitled "Electrocardiography Monitor," No. D717955, issued on Nov. 18, 2014, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 5:
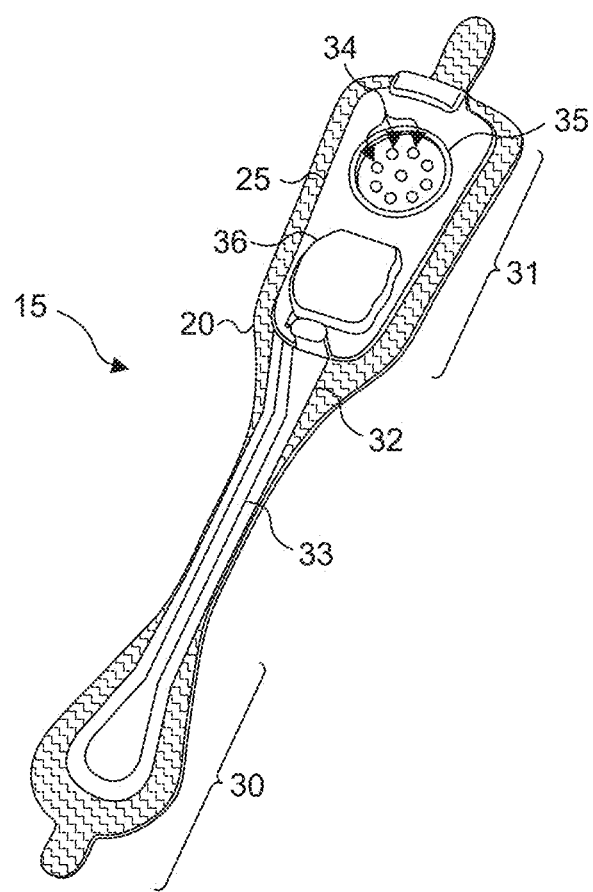
FIG. 5 is a perspective view showing the extended wear electrode patch of FIG. 3 without a monitor recorder inserted.

During use, the electrode patch 15 is first adhered to the skin in the sternal region. FIG. 5 is a perspective view showing the extended wear electrode patch 15 of FIG. 3 without a monitor recorder 14 inserted. A flexible circuit 32 is adhered to each end of the flexible backing 20. A distal circuit trace 33 and a proximal circuit trace (not shown) electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

Figure 6:
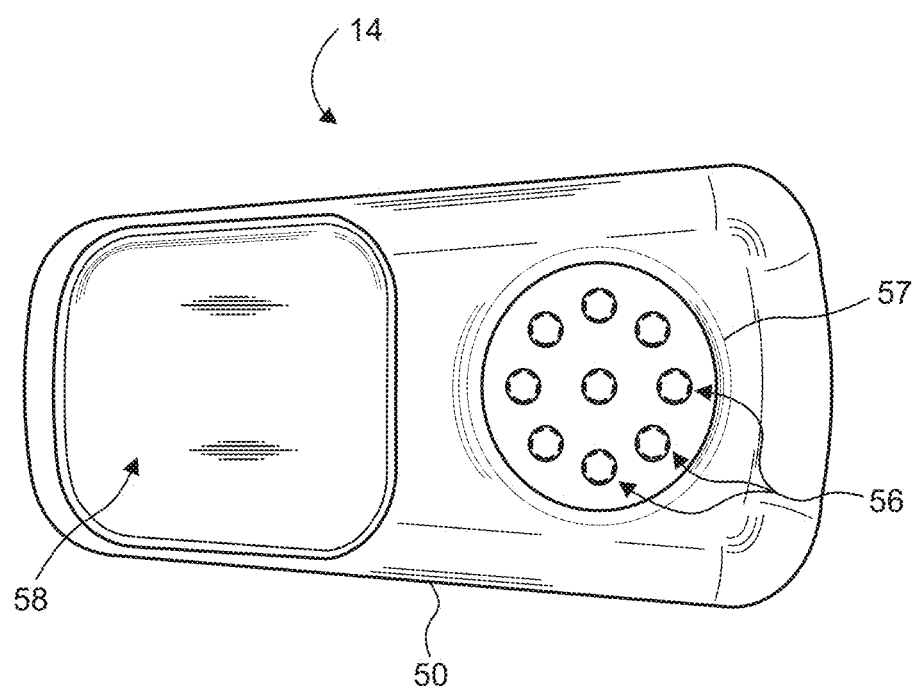
FIG. 6 is a bottom plan view of the monitor recorder of FIG. 3.

The monitor recorder 14 draws power externally from the battery provided in the non-conductive receptacle 25, thereby uniquely obviating the need for the monitor recorder 14 to carry a dedicated power source. FIG. 6 is a bottom plan view of the monitor recorder 14 of FIG. 3. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 7:
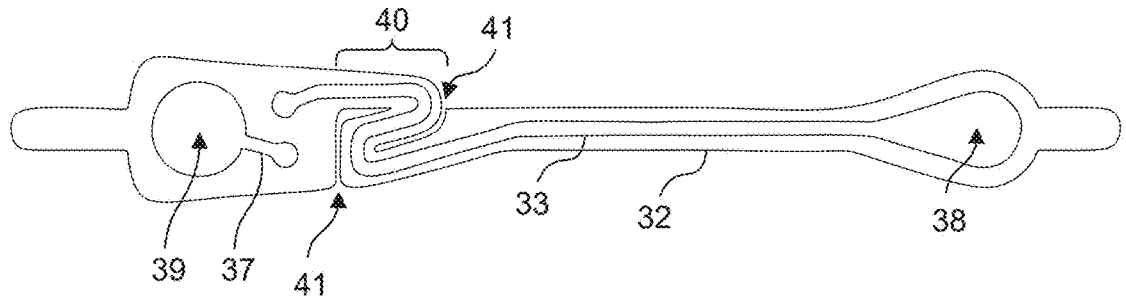
FIG. 7 is a top view showing the flexible circuit of the extended wear electrode patch of FIG. 3 when mounted above the flexible backing.

Unlike the flexible backing 20, the flexible circuit 32 is only able to bend and cannot stretch in a planar direction. The flexible circuit 32 can be provided either above or below the flexible backing 20. FIG. 7 is a top view showing the flexible circuit 32 of the extended wear electrode patch 15 of FIG. 3 when mounted above the flexible backing 20. A distal ECG electrode 38 and proximal ECG electrode 39 are respectively coupled to the distal and proximal ends of the flexible circuit 32. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 8:
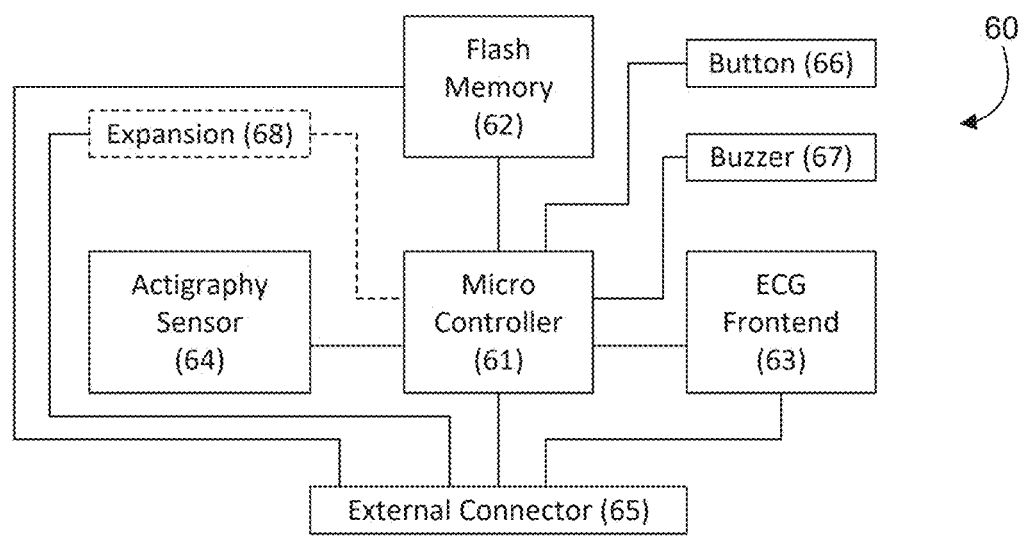
FIG. 8 is a functional block diagram showing the component architecture of the circuitry of the monitor recorder of FIG. 3.

ECG monitoring and other functions performed by the monitor recorder 14 are provided through a micro controlled architecture. FIG. 8 is a functional block diagram showing the component architecture of the circuitry 60 of the monitor recorder 14 of FIG. 3. The circuitry 60 is externally powered through a battery provided in the non-conductive receptacle 25 (shown in FIG. 5). Both power and raw ECG signals, which originate in the pair of ECG electrodes 38, 39 (shown in FIG. 7) on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and which physically and electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or download station (not shown), follow the same electrical pin assignment convention to facilitate interoperability. The external connector 65 also serves as a physical interface to a download station that permits the retrieval of stored ECG monitoring data, communication with the monitor recorder 14, and performance of other functions.

Operation of the circuitry 60 of the monitor recorder 14 is managed by a microcontroller 61. The micro-controller 61 includes a program memory unit containing internal flash memory that is readable and writeable. The internal flash memory can also be programmed externally. The microcontroller 61 draws power externally from the battery provided on the electrode patch 15 via a pair of the electrical contacts 56. The microcontroller 61 connects to the ECG front end circuit 63 that measures raw cutaneous electrical signals and generates an analog ECG signal representative of the electrical activity of the patient's heart over time.

The circuitry 60 of the monitor recorder 14 also includes a flash memory 62, which the micro-controller 61 uses for storing ECG monitoring data and other physiology and information. The flash memory 62 also draws power externally from the battery provided on the electrode patch 15 via a pair of the electrical contacts 56. Data is stored in a serial flash memory circuit, which supports read, erase and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

The circuitry 60 of the monitor recorder 14 further includes an actigraphy sensor 64 implemented as a 3-axis accelerometer. The accelerometer may be configured to generate interrupt signals to the microcontroller 61 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses.

The microcontroller 61 includes an expansion port that also utilizes the communications bus. External devices, separately drawing power externally from the battery provided on the electrode patch 15 or other source, can interface to the microcontroller 61 over the expansion port in half duplex mode. For instance, an external physiology sensor can be provided as part of the circuitry 60 of the monitor recorder 14, or can be provided on the electrode patch 15 with communication with the micro-controller 61 provided over one of the electrical contacts 56. The physiology sensor can include an SpO$_2$ sensor, blood pressure sensor, temperature sensor, respiratory rate sensor, glucose sensor, airflow sensor, volumetric pressure sensing, or other types of sensor or telemetric input sources. In a further embodiment, a wireless interface for interfacing with other wearable (or implantable) physiology monitors, as well as data offload and programming, can be provided as part of the circuitry 60 of the monitor recorder 14, or can be provided on the electrode patch 15 with communication with the micro-controller 61 provided over one of the electrical contacts 56.

Finally, the circuitry 60 of the monitor recorder 14 includes patient-interfaceable components, including a tactile feedback button 66, which a patient can press to mark events or to perform other functions, and a buzzer 67, such as a speaker, magnetic resonator or piezoelectric buzzer. The buzzer 67 can be used by the microcontroller 61 to output feedback to a patient such as to confirm power up and initiation of ECG monitoring. Still other components as part of the circuitry 60 of the monitor recorder 14 are possible.

Figure 9:
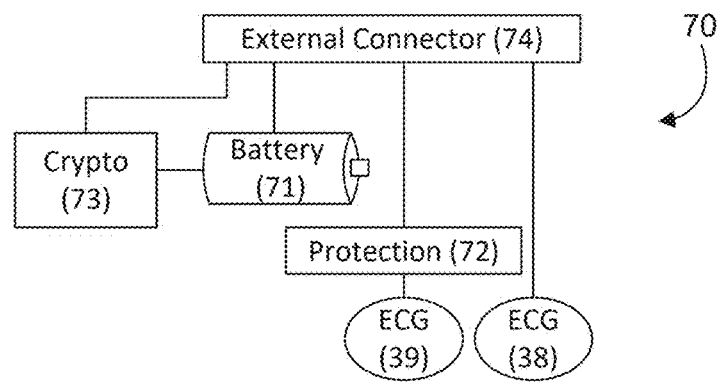
FIG. 9 is a functional block diagram showing the circuitry of the extended wear electrode patch of FIG. 3.

While the monitor recorder 14 operates under micro control, most of the electrical components of the electrode patch 15 operate passively. FIG. 9 is a functional block diagram showing the circuitry 70 of the extended wear electrode patch 15 of FIG. 3. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, the locating of the battery 71 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Finally, the architecture of the monitor recorder 14 is open, in that other physiology sensors or components can be added by virtue of the expansion port of the microcontroller 61. Requiring those additional sensors or components to draw power from a source external to the monitor recorder 14 keeps power considerations independent of the monitor recorder 14. Thus, a battery of higher capacity could be introduced when needed to support the additional sensors or components without effecting the monitor recorders circuitry 60.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14.

Figure 10:
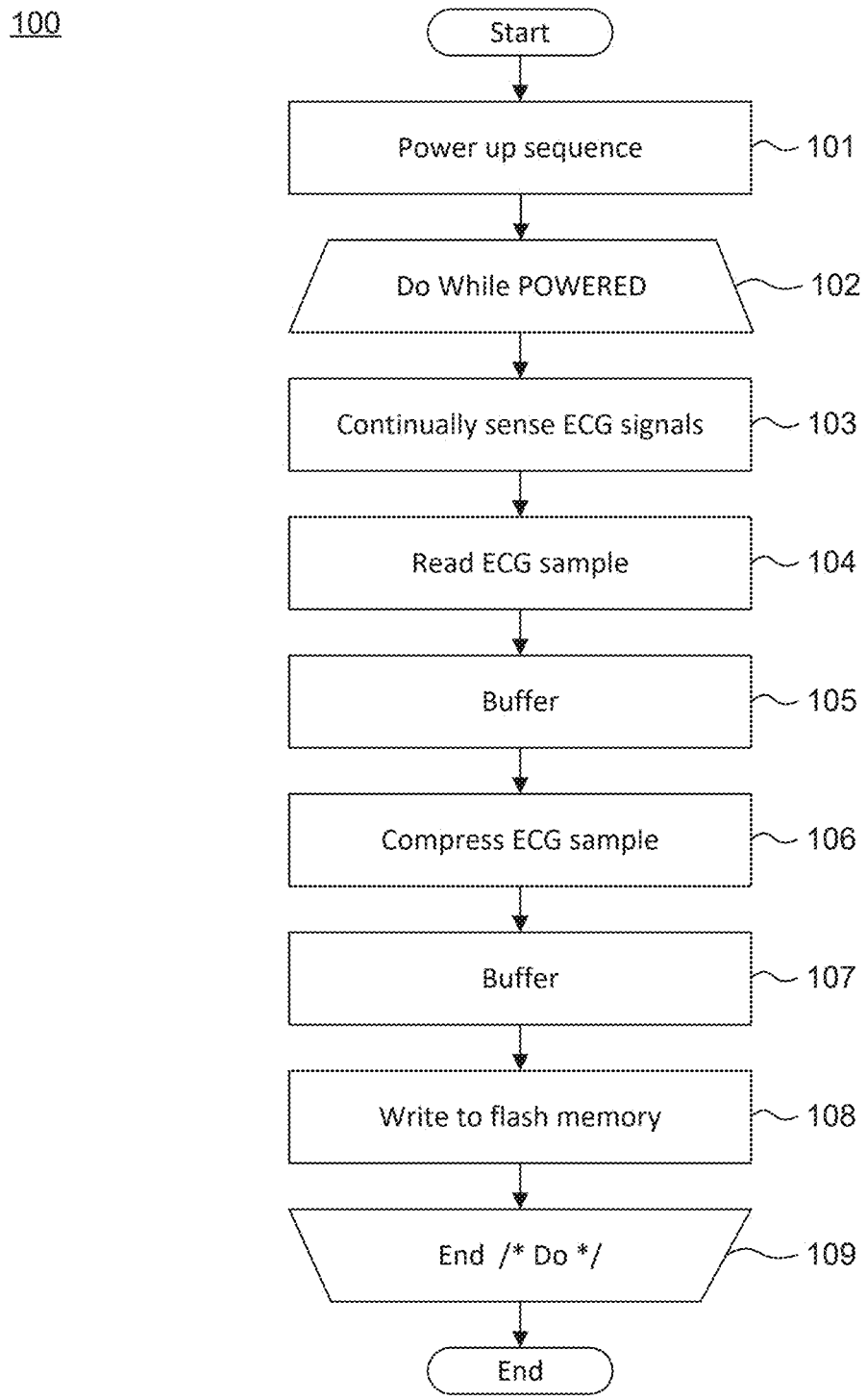
FIG. 10 is a flow diagram showing a monitor recorder-implemented method for monitoring ECG data for use in the monitor recorder of FIG. 3.

The monitor recorder 14 continuously monitors the patient's heart rate and physiology. FIG. 10 is a flow diagram showing a monitor recorder-implemented method 100 for monitoring ECG data for use in the monitor recorder 14 of FIG. 3. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Figure 11:
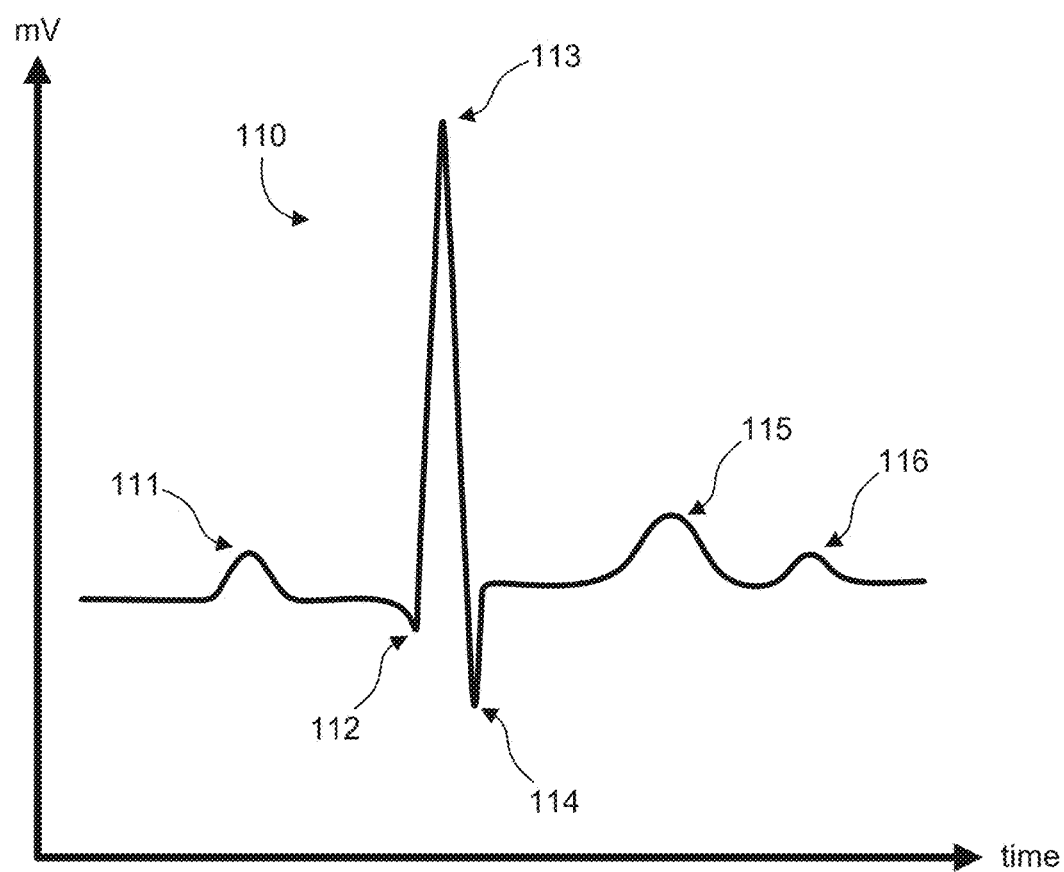
FIG. 11 is a graph showing, by way of example, a typical ECG waveform.

Following satisfactory completion of the power up sequence, an iterative processing loop (steps 102-109) is continually executed by the microcontroller 61. During each iteration (step 102) of the processing loop, the ECG frontend 63 (shown in FIG. 8) continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal output front end 63. FIG. 11 is a graph showing, by way of example, a typical ECG waveform 110. The x-axis represents time in approximate units of tenths of a second. The y-axis represents cutaneous electrical signal strength in approximate units of millivolts. The P-wave 111 has a smooth, normally upward, that is, positive, waveform that indicates atrial depolarization. The QRS complex usually begins with the downward deflection of a Q wave 112, followed by a larger upward deflection of an R-wave 113, and terminated with a downward waveform of the S wave 114, collectively representative of ventricular depolarization. The T wave 115 is normally a modest upward waveform, representative of ventricular depolarization, while the U wave 116, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the extended wear ambulatory electrocardiography and physiological sensor monitor described herein is medically unique and important. The long-term observation of these ECG indicia, as provided through extended wear of the wearable monitor 12, provides valuable insights to the patient's cardiac function and overall well-being.

Each sampled ECG signal, in quantized and digitized form, is temporarily staged in buffer (step 105), pending compression preparatory to storage in the flash memory 62 (step 106). Following compression, the compressed ECG digitized sample is again buffered (step 107), then written to the flash memory 62 (step 108) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

While the invention has been particularly shown and described as referenced to the embodiments thereof, those skilled in the art will understand that the foregoing and other changes in form and detail may be made therein without departing from the spirit and scope.

What is claimed is:

1. An electrocardiography monitor, comprising:
    a battery;
    a non-conductive receptacle configured to house the battery;
    a housing, wherein the housing engages the non-conductive receptacle and the non-conductive receptacle is configured to receive the housing, wherein the battery is positioned between the housing and a bottom surface of the non-conductive receptacle;
    an electrographic circuit to measure electrographic signals;
    a distal electrocardiography electrode disposed at a distal end of a flexible circuit and a proximal electrocardiography electrode disposed at a proximal end of the flexible circuit, wherein the flexible circuit is coupled to a flexible backing, and wherein the flexible backing is configured to adhere to skin of a patient's chest; and
    a microcontroller disposed within the housing, wherein the microcontroller communicates with the electrocardiographic circuit to record the electrocardiographic signals.

2. The electrocardiography monitor according to claim 1, comprising:
    a seal coupling surrounding electrical contacts, wherein the electrical contacts protrude from the bottom surface of the housing to connect to the battery to power the microcontroller.

3. The electrocardiography monitor according to claim 1, further comprising:
    electrical contacts to establish an electrical connection with the distal electrocardiography electrode and the proximal electrocardiography electrode for sensing the electrocardiographic signals.

4. The electrocardiography monitor according to claim 1, wherein the housing is shaped for placement over the battery.

5. The electrocardiography monitor according to claim 1, further comprising:
    circuitry for an actigraphy sensor.

6. The electrocardiography monitor according to claim 5, wherein the actigraphy sensor generates interrupt signals to the microcontroller based on a position of the housing.

7. The electrocardiography monitor according to claim 1, wherein the housing comprises polycarbonate, acrylonitrile butadiene styrene ("ABS"), or an alloy of polycarbonate and ABS.

8. The electrocardiography monitor according to claim 1, further comprising:
flash memory configured to store the electrocardiographic signals.

9. The electrocardiography monitor according to claim 1, further comprising:
an expansion port via which an external device interfaces to the microcontroller.

10. The electrocardiography monitor according to claim 9, wherein the external device comprises a physiological sensor.

11. An electrocardiography monitor assembly, comprising:
a battery compartment formed on a bottom surface of a non-conductive receptacle, wherein a battery is located in the battery compartment;
a housing, wherein the non-conductive receptacle is configured to receive the housing, and wherein the battery compartment is positioned between the housing and the bottom surface of the non-conductive receptacle;
an electrographic circuit to measure electrocardiographic signals;
a distal electrocardiography electrode disposed at a distal end of a flexible circuit and a proximal electrocardiography electrode disposed at a proximal end of the flexible circuit, wherein the flexible circuit is coupled to a flexible backing, and wherein the flexible backing is configured to adhere to skin of a patient's chest; and
a microcontroller disposed within the housing, wherein the microcontroller communicates with the electrocardiographic circuit to record the electrocardiographic signals into memory.

12. The electrocardiography monitor assembly according to claim 11, comprising:
a seal coupling surrounding electrical contacts.

13. The electrocardiography monitor assembly according to claim 11, further comprising:
electrical contacts to establish an electrical connection with the distal electrocardiography electrode and the proximal electrocardiography electrode for sensing the electrocardiographic signals.

14. The electrocardiography monitor assembly according to claim 11, wherein the housing is shaped to fit over the battery.

15. The electrocardiography monitor assembly according to claim 11, further comprising:
circuitry for an actigraphy sensor comprised within the housing.

16. The electrocardiography monitor assembly according to claim 15, wherein the actigraphy sensor generates interrupt signals to the microcontroller based on a position of the housing.

17. The electrocardiography monitor assembly according to claim 11, wherein the housing comprises polycarbonate, ABS, or an alloy of polycarbonate and ABS.

18. The electrocardiography monitor assembly according to claim 11, further comprising:
flash memory configured to store the electrocardiographic signals.

19. The electrocardiography monitor assembly according to claim 11, further comprising:
an expansion port comprised in the circuitry via which an external device interfaces to the microcontroller.

20. The electrocardiography monitor assembly according to claim 19, wherein the external device comprises a physiological sensor.

* * * * *